United States Patent

Simon

[11] 4,117,716
[45] Oct. 3, 1978

[54] DENSITOMETER APPARATUS

[75] Inventor: Frank N. Simon, Bloomington, Minn.

[73] Assignee: Honeywell Inc., Minneapolis, Minn.

[21] Appl. No.: 634,689

[22] Filed: Nov. 24, 1975

Related U.S. Application Data

[63] Continuation of Ser. No. 479,926, Jun. 17, 1974, abandoned.

[51] Int. Cl.² .............................................. G01N 11/16
[52] U.S. Cl. ........................................ 73/32 A; 73/54
[58] Field of Search .................... 73/24, 67, 67.1, 67.2, 73/32 A, 67.5 R, 67.8 R, 71.5 US, 54, 59

[56] References Cited

U.S. PATENT DOCUMENTS

| | | | |
|---|---|---|---|
| 2,903,884 | 9/1959 | Kritz | 73/32 |
| 3,353,400 | 11/1967 | Schafft | 73/24 |
| 3,562,792 | 2/1971 | Berlincourt et al. | 310/8 |
| 3,794,866 | 2/1974 | McElroy et al. | 73/71.5 U |

FOREIGN PATENT DOCUMENTS 830,463  3/1960  United Kingdom .................. 73/59

Primary Examiner—Richard E. Aegerter
Assistant Examiner—Willis Little
Attorney, Agent, or Firm—Theodore F. Neils

[57] ABSTRACT

A densitometer and sonic velocimeter are provided through use of a transducer to provide energy transductions and for providing vibratory energy. In this way, longitudinal wave energy can be imparted to the surrounding fluid. Indications from the transducer provide a representation of the fluid density.

16 Claims, 3 Drawing Figures

U.S. Patent   Oct. 3, 1978   4,117,716 a — LENGTH
b — WIDTH
k — WAVENUMBER a — EFFECTIVE RADIUS
k — WAVENUMBER 4,117,716

DENSITOMETER APPARATUS

This is a continuation of application Ser. No. 479,926, filed June 17, 1974 now abandoned.

BACKGROUND OF THE INVENTION

This invention related to densitometers which can provide a representation of the density of the adjacent fluid portions and a representation of the sonic velocity in adjacent fluid portions. Particularly related are devices wherein a transducer is used to determine these representations by imparting longitudinal wave energy to the adjacent fluid portions.

Density of a fluid is generally determinable by measuring the mass of a known volume of the fluid. This can be accomplished by the use of the balance and by the use of a calibrated container. Another method is to use a mechanically vibrating body which includes a container of a known volume to contain the fluid. By noting the resonant frequency of the vibrating body with and without a fluid mass in the container, the density of the fluid may be determined. For measurement convenience, determining the density of the fluid without resort to a calibrated volume container and having the density information contained in an electrical signal would be desirable.

SUMMARY OF THE INVENTION

A sensor is provided in which a transducer therein provides an energy transduction from one form of energy to another and, in doing so, has surfaces of the transducer placed in motion in directions such that longitudinal wave energy is imparted to those portions of the fluid of interest adjacent to these surfaces, within a limited range of conditions for some purposes. This transducer has electrical input terminals to which oscillator circuitry means are attached whereby the circuit oscillation frequency is a resonant frequency associated with the moving surfaces when submerged in the fluid. This frequency can be determined by a value of the effect of the electrical impedance occurring between the electrical input terminals.

The transducer provides an output or outputs indicative of the density of the fluid of interest in the adjacent portions of the fluid of interest and the velocity of sound therein. This output may be used with display and/or computation means or other output sensing means.

The transduction of energy forms may be one of a sequence, such as to provide a voltage transformation between the electrical input terminals and electrical output terminals by use of a piezoelectric transformer as a transducer.

DESCRIPTION OF THE PREFERRED EMBODIMENTS

Figure 1:
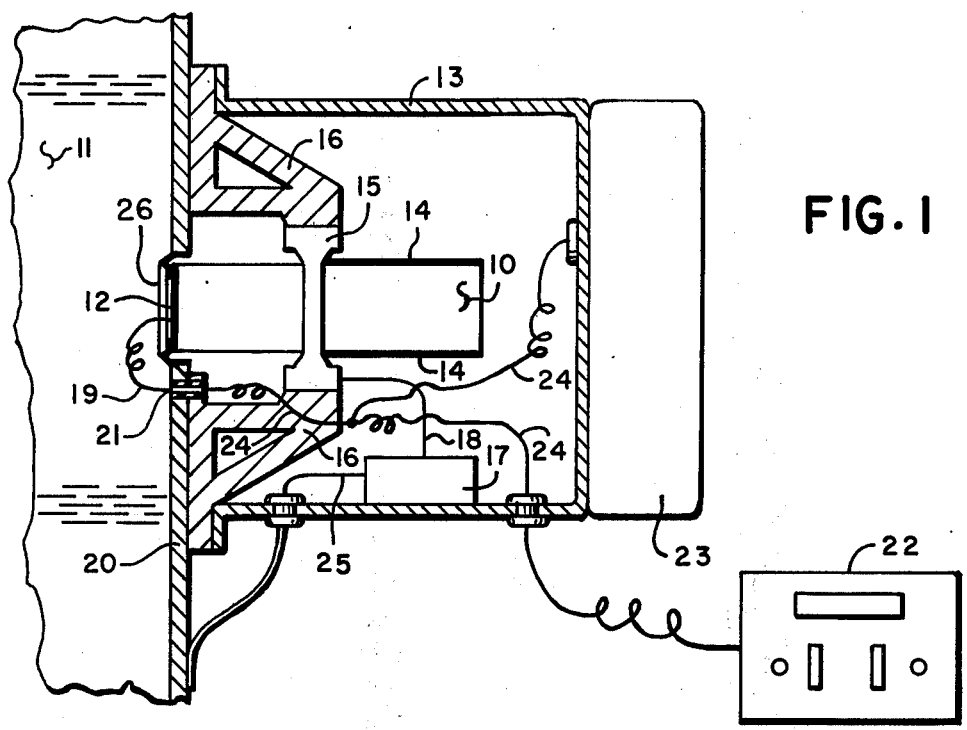
FIG. 1 shows an embodiment of the present invention.

When a vibrating body is provided in a fluid, the vibratory motion of the body can generally apply both shear stresses and normal stresses to the fluid. The applied shear stresses and the applied normal stresses lead to acoustic waves occurring in the fluid, both shear and longitudinal waves. The reactive force of the fluid on the vibrating body loads the body, damping its motions, with the result that the vibratory characteristics of the body are altered. This reactive force of the fluids must be equaled by the force and stresses applied to the fluid by the vibrating body.

The fluid reactive normal force on the vibrating body, being a normal stress of the fluid integrated over the surface area of the vibrating body, is related to the parameters of the surrounding fluid such as the fluid density, the fluid compressibility and so forth. This relationship between the altered vibrating body characteristics, due to the normal reactive force of the fluid thereon, and the fluid parameters provides a basis for determining some of these fluid parameters through determining the changes in the parameters describing the vibrating body, these changes being a result of altering the vibrating characteristics of the body due to loading it with a fluid.

The fluid reactive shear force on the vibrating body, being the shear stress of the fluid integrated over the surface area of the vibrating body, is also related to the parameters of the fluid, but these relationships differ from those describing the fluid reactive normal forces and the fluid parameters. This shear reactive force, accordingly, alters the vibrating characteristics of the vibrating body in a given fluid differently than does the reactive normal force.

From one analytical point of view, the electrical effects in an electrically driven, vibrating body of both the fluid reactive normal force and of the fluid reactive shear force acting on this body can be described by an equivalent "electrical" circuit through the use of ideal transformers and the use of generalized impedances for the elements of the equivalent circuit. Generally, both resistive and reactive generalized impedance elements, serving as radiation impedances for both shear and longitudinal wave energy radiations, are found to be needed to represent the vibrating body in the fluid of interest. This indicates that power dissipation will occur, i.e. energy will be imparted to the fluid via the longitudinal and shear waves initiated therein by the vibrating body, and that a shift in resonant frequency will occur dependent upon values required for these generalized impedance elements to represent adequately the vibrating body as submerged in a fluid.

The values of these generalized impedance elements will be functions of the fluid parameters since these impedances represent the vibrating body as it is subjected to the shear and normal reactive forces of the fluid thereon. From another view, the impedances represent the vibrating body structural parameters as modulated by the surrounding fluid to an extent determined by the parameters of the fluid, which structural parameter modulation in turn modulates the acoustic vibratory energy in the crystal. The ideal transformers represent transductions in energy forms in the vibrating body, for instance from input electrical energy to acoustical vibrating energy. As these generalized impedances change in value with changing fluid parameters, the effective input impedance at the electrical input terminals changes accordingly.

If the vibrating body is configured in such a manner that the only surfaces which are in contact with the fluid of interest are those surfaces capable of imparting longitudinal wave energy to the fluid and only insubstantial surfaces which impart shear wave energy to the fluid are in contact therewith, the vibrating body will essentially face only a longitudinal acoustic impedance. In this situation fluid viscosity is not an important parameter of the fluid affecting the vibrating body but fluid density and fluid compressibility or equivalently, the velocity of sound in the fluid, are important parameters affecting the vibrating body. These parameters should be conveniently measured if a signal indicating the effect of these parameters on the vibratory body, particularly an electrical signal, could be obtained.

The present invention contemplates accomplishing this by use of a piezoelectric transformer. This transformer can be viewed for analytical purposes as an equivalent "electrical" circuit, having an ideal transformer for converting electrical energy to acoustical vibratory energy and a second ideal transformer for converting acoustical vibratory energy back to electrical energy. Various generalized impedances would also be needed to represent the piezoelectric transformer including radiation impedances connected between the two ideal transformers. The use of a piezoelectric transformer provides an output voltage signal of a substantial magnitude which needs little or no amplification for further processing and the properties of this signal provide a convenient indication of fluid density of a fluid of interest in contact with the piezoelectric transformer and of the velocity of sound in this fluid.

FIG. 1 shows a piezoelectric transformer, 10, in the shape of a rectangular bar of piezoelectric material provided, in part, against a fluid, 11. The part or portion serving as an interface between transformer 10 and in the fluid 11 is the end face of the secondary portion of the transformer which has thereon an output terminal, 12. The primary end of the transformer is located outside fluid 11 within protective cover 13. This end of the transformer has input driving electrodes, 14, located thereon which cover the entire length-width faces of the transformer primary, the width dimension being perpendicular to the plane of the drawing, with the electrode 14 separated by the thickness of the piezoelectric transformer. Piezoelectric transformer 10 is supported in a mount, 15, which in turn is supported by mounting plate, 16. Driving electronics, 17, are connected to the input terminals 14 through mount 15 and an input cable, 18. The output terminal 12 supplies an output voltage signal through an output cable, 19, which passes through a fluid reservoir wall, 20, and mounting plate 16 via an insulated conducting post, 21. This output voltage signal is supplied to remote electronics, 22, and local electronics, 23, via distribution cable 24. The driving electronics 17 have power supplied thereto by a power input cable, 25.

A very lightweight and compliant insulating membrane, 26, is attached to the edge of the electrode 12 and is attached to the reservoir wall 20. This membrane must be strong enough to withstand the pressure of the fluid but yet must be so lightweight and compliant that it does not too substantially dampen the motion of the piezoelectric transformer 10. Too much damping will lead to difficulties in obtaining an output signal which can distinguish changing fluid parameters. The end face of piezoelectric transformer 10 with terminal 12 thereon should be as large in area with respect to the effective area of the membrane 26 as possible.

The design of piezoelectric transformer 10 and its mounting arrangement results in the motion of the secondary portion, the only portion which is in contact with the fluid when the transformer is in operation, being an oscillating, reciprocal motion along the length of the transformer 10. Therefore, the end face of the secondary portion of piezoelectric transformer 10 with terminal 12 thereon is placed in motion only in a direction normal to this end face and as a result, substantially only longitudinal wave energy is imparted to fluid 11. The frequency of operation of the transformer, its resonant frequency when against fluid 11, is primarily controlled by the length dimension of the transformer so that the area of the end face of the secondary portion of the transformer can be varied at will to a substantial extent.

For proper results, mount 15 and mounting plate 16 should be rigid and mount 15 should be located at or near the node of vibratory motion of the piezoelectric transformer. Mounting the transformer in this method prevents the mount from affecting the damping force on the transformer too strongly.

Electronics 17 includes an oscillator circuit to supply voltage to input terminals 14. The oscillator electronics is such that the frequency of oscillation of the voltage applied to input terminals 14 is set by the effective input impedance occurring between input terminals 14 which impedance becomes a functional impedance in the oscillator circuit, much in the manner of a crystal controlled oscillator with piezoelectric transformer 10 being the controlling crystal. An oscillator circuit with a square wave voltage provided at the input terminals of the transformer to result in a sinusoidal wave voltage at the transformer output which can be picked up by a feedback loop to form the oscillator is a particularly effective driving circuit.

The oscillation frequency of the circuit will occur at a resonant frequency of the transformer as placed against fluid 11, this resonant frequency being the frequency at which the effective input impedance of the transformer becomes purely resistive. Analytically, this effective input impedance is determined from the generalized impedances representing the piezoelectric transformer against fluid 11 as they are reflected across the ideal input transformer representing the transduction from input electrical energy to acoustic vibratory energy. In the present embodiment there are no significant electrical impedances on the primary side of this ideal input transformer to consider. As a result, piezoelectric transformer 10 is always at its resonant frequency as determined by both the characteristics of the transformer and the effects on the transformer of fluid 11 against it.

Use of a variable frequency electrical wave generator to find the resonant frequency (at which frequency not only is the effective input impedance purely resistive but also the output voltage is at maximum amplitude) by use of sinusoidal wave and to drive transformer 10 at this frequency when submerged is also possible but is not as convenient. The resonant frequency can be determined most conveniently in this method by monitoring the output voltage signal at terminal 12 for the operating transformer and adjusting the wave generator frequency until this voltage signal has a maximum amplitude. Use of a square wave from a generator can eliminate any need to find the resonant frequency since the resonant frequency would substantially be the only frequency excited and present at the transformer output.

An analysis which assumes that the piezoelectric transformer is a rectangular bar having no shear occurring within the piezoelectric material thereof in operation, that the surfaces in the fluid impart primarily longitudinal wave energy and that a one dimensional analysis is sufficient results in a voltage output amplitude relationship and a frequency shift relationship which are each two relatively complicated functions of the fluid density and the fluid sonic velocity, if no further restrictions are placed on the preceding piezoelectric transformer. While these relationships can be solved in some manner for fluid density and fluid sonic velocity, simpler relationships would be more convenient. Further, without any added restrictions on the preceding piezoelectric transformer, longitudinal waves will occur in the fluid. Because longitudinal waves can be supported over substantial distances by most fluids, there is a substantial possibility of reflections occurring to bring these longitudinal waves back to the piezoelectric transformer surfaces. These reflections alter the relationships between the voltage output signal from the piezoelectric transformer and the fluid parameters. In a few instances, these relationships can be derived to allow calculation of the fluid density and the fluid sonic velocity. In other instances, an empirical correction factor can be found to allow determination of the fluid density and the fluid sonic velocity. Often, this will not be possible and it would be convenient to avoid these reflected waves.

The longitudinal acoustic impedance has some special properties which are found to generally hold whatever the shape of the acoustically radiating body which properties can be exploited to permit obtaining simpler relationships and removing the possibility of reflection. Both the resistive and the reactive portions of the longitudinal impedance approach zero as the ratio of two parameters becomes quite small, one parameter being a dimension representing the extent of the surface imparting longitudinal wave energy to the fluid and the other parameter being the wavelength of the longitudinal wave energy. If the ratio is very small so the impedance is very small, no longitudinal wave energy is imparted to the fluid. The normally vibrating surface area of the vibrating body concerned is negligible.

However, the resistive portion and the reactive portion of the impedance approach zero at different rates of change with respect to the preceding ratio as this ratio becomes small, with the resistive portion approaching zero much more rapidly than does the reactive portion. This characteristic provides a range of values for this ratio in which the reactive portion of the longitudinal acoustic impedance is significant while the resistive portion is negligible. Hence, in this range no substantial amount of longitudinal waves occur in the fluid to carry energy away but instead energy is traded back and forth between the fluid and the surface driving the fluid. The longitudinal acoustic impedance has been calculated for several kinds of longitudinal wave energy radiating bodies, and this relationship between the resistive portion and the reactive portion has been found to hold more or less generally.

Figure 2:
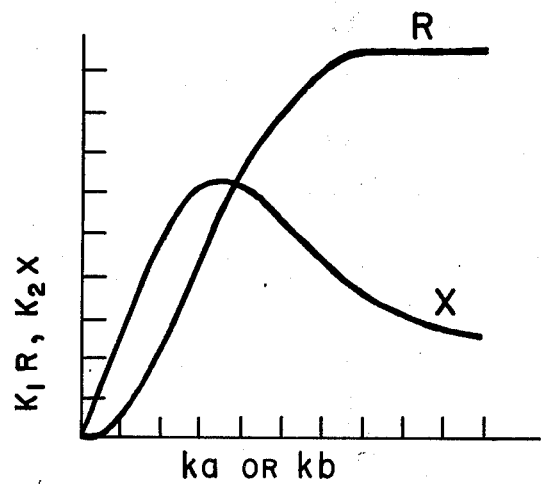
FIG. 2 shows a graph of the components of the longitudinal acoustic impedance faced by a rectangular piston set in a plane imparting longitudinal wave energy to adjacent fluid portions.
Figure 3:
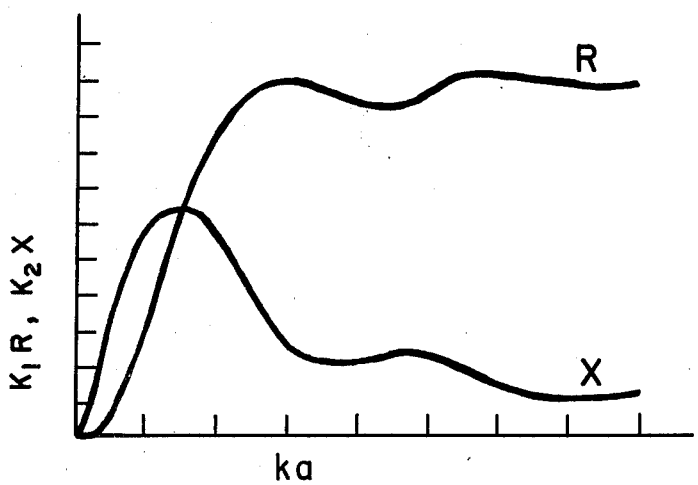
FIG. 3 shows a similar graph for a piston set in a sphere.

FIGS. 2 and 3 show examples of the results of these calculations for two substantially differently shaped radiating bodies. FIG. 2 shows graphs of curves which are proportional to the resistive and to the reactive components of the longitudinal acoustic impedance facing a rectangular piston having a flat face set in a plane. The curve related to the resistive portion is labeled with an R and the curve related to the reactive portion is labeled with an X. FIG. 3 shows a graph of the resistive portion, labeled R, and the reactive portion, labeled X, of the longitudinal acoustic impedance facing an acoustically radiating portion of a sphere, the portion determined by a plane intersecting with the sphere. The substantial geometrical difference between these acoustically radiating bodies and the settings they are in can be seen to have rather little effect on the relative relationship between the resistive and the reactive components as the extent dimension/wavelength ratio becomes small.

An acoustically radiating body, then, can be designed so that the longitudinal wave energy imparting surfaces thereof have an extent dimension/wavelength ratio small enough so that the longitudinal acoustic impedance facing these surfaces is primarily reactive. Again, any shear wave energy imparting surfaces have a sufficiently small area so as not to substantially affect the relationship between the fluid parameters and the output voltage signal.

An analysis which assumes that the piezoelectric transformer is a rectangular bar which has no shear occurring within the piezoelectric material of the bar itself, that the surfaces of the piezoelectric transformer imparts primarily longitudinal wave energy to the fluid and that a one dimensional analysis is sufficient results in two relationships describing the output voltage signal for the piezoelectric transformer for a properly restricted parameter ratio. The first relationship is a voltage amplitude relationship which is as follows:

$$V_v - V = K_1 (\rho f_o/c)$$

$\rho$ = fluid density of fluid of interest
$c$ = sonic velocity of fluid of interest
$f_o$ = resonant frequency in fluid of interest
$V_v$ = output voltage amplitude in vacuum
$V$ = output voltage amplitude in fluid of interest
$K_1$ = calibration The second relationship is a frequency shift relationship and is as follows:

$$f_{ov} - f_o = K_2 f_o \rho$$

$\rho$ = fluid density of fluid of interest
$f_{ov}$ = resonant frequency in vacuum
$f_o$ = resonant frequency in fluid of interest
$K_2$ = calibration The constants in the above equations can be determined through a calibration procedure. To determine the constants in the first equation, the transformer must be operated in a vacuum and in a fluid of known fluid density and known fluid sonic velocity or, alternatively, the transformer must be operated in two different fluids having known fluid density and fluid sonic velocity. In either situation, the output voltage signal amplitude and the oscillation frequency thereof must be measured in each medium. The constants in the second equation can be determined similarly.

The output voltage signal from terminal 12 of piezoelectric transformer 10 can be transmitted through the computation/display electronics 22 to perform such calculations and to display the results. This is true also, of course, of local electronics 23. Alternatively, various other ways of data reduction can be used to provide fluid density and fluid sonic velocity from the output voltage signal appearing at terminal 12.

The embodiments of the invention in which an exclusive property or right is claimed are defined as follows:

1. A sensor capable of providing a representation of density of a fluid and a representation of sonic velocity in a fluid, said sensor comprising:
   a piezoelectric transformer, having electrical terminals therein serving as input terminals and output terminals, said transformer having surfaces thereof placed in motion in directions in which they are capable of imparting longitudinal wave energy to those portions of said fluid sufficiently near said surfaces;
   oscillator circuitry means connected to provide an oscillating electrical signal at said input terminals; and
   output voltage sensing means connected to sense an output voltage signal provided between said output terminals to provide at least one of said representations.

2. The system of claim 1 wherein said oscillator circuitry means includes a variable frequency electrical wave generator operating in a manner which excites a resonance in said motion.

3. The system of claim 1 wherein said oscillator circuitry means includes an oscillator circuit which has said transformer operating as a functional element therein in a manner which excites a resonance in said motion.

4. The system of claim 1 wherein said output sensing means includes computation apparatus.

5. The system of claim 1 wherein a mount supporting said transformer is joined to said transformer substantially at a node in said motion of said surfaces.

6. The system of claim 1 wherein said transformer is shaped as a rectangular bar.

7. A sensor capable of providing a representation of density of a fluid and a representation of sonic velocity in a fluid, said sensor comprising:
   an electrical transducer, having electrical terminals therein with at least some serving as input terminals, said transducer providing a transduction between energy types therein and with said transducer, in effecting said transduction, having surfaces thereof placed in motion in directions in which they are capable of imparting longitudinal wave energy to those portions of said fluid sufficiently near said surfaces, said transducer constructed such that said surfaces face a longitudinal acoustic radiation impedance in said fluid which is substantially purely reactive;
   oscillator circuitry means connected to provide an oscillating electrical signal at said input terminals; and
   output sensing means connected to some of said electrical terminals to sense an output indication to provide at least one of said representations.

8. The system of claim 7 wherein said transduction is effected between said input terminals and some of said electrical terminals serving as output terminals with one of said output terminals being other than one of said input terminals, said transduction plus at least one other providing a voltage transformation such that said output indication is an output voltage signal provided between said output terminals.

9. The system of claim 7 wherein said oscillator circuitry means includes a variable frequency electrical wave generator operating in a manner which excites a resonance in said motion, said motion being vibratory.

10. The system of claim 7 wherein said oscillator circuitry means includes an oscillator circuit which has said transducer operating as a functional element therein in a manner which excites a resonance in said motions, said motions being vibratory.

11. The system of claim 7 wherein said output sensing means includes computation apparatus.

12. The system of claim 7 wherein there is a node in said motion of said surfaces, said motions being vibratory.

13. The system of claim 8 wherein said voltage transformation is accomplished by use of a piezoelectric effect.

14. The system of claim 12 wherein a mount supporting said transducer is joined to said transducer substantially at said node.

15. The system of claim 13 wherein said transducer is a piezoelectric transformer.

16. The system of claim 15 wherein said transformer is shaped as a rectangular bar and said surfaces are approximately only end surfaces of said bar.

* * * * *